United States Patent
Pallett et al.

(10) Patent No.: US 6,878,675 B2
(45) Date of Patent: Apr. 12, 2005

(54) HERBICIDAL COMPOSITIONS

(75) Inventors: Ken Pallett, Königstein (DE); Ashley Slater, Ongar (GB)

(73) Assignee: Bayer CropScience S.A., Lyons (FR)

( * ) Notice: Subject to any disclaimer, the term of this patent is extended or adjusted under 35 U.S.C. 154(b) by 0 days.

(21) Appl. No.: 10/380,362

(22) PCT Filed: Sep. 17, 2001

(86) PCT No.: PCT/EP01/10693

§ 371 (c)(1),
(2), (4) Date: Oct. 2, 2003

(87) PCT Pub. No.: WO02/21922

PCT Pub. Date: Mar. 21, 2002

(65) Prior Publication Data

US 2004/0072691 A1 Apr. 15, 2004

(30) Foreign Application Priority Data

Sep. 18, 2000 (GB) .............................................. 0022833

(51) Int. Cl.⁷ ........................ A01N 43/824; A01N 33/22
(52) U.S. Cl. ........................ 504/139; 504/263; 504/350
(58) Field of Search ................................ 504/139, 263, 504/350

(56) References Cited

U.S. PATENT DOCUMENTS

| | | | |
|---|---|---|---|
| 4,968,342 A | 11/1990 | Forster et al. | |
| 5,506,195 A | 4/1996 | Ensminger et al. | |
| 2004/0102321 A1 | 5/2004 | Feucht et al. | |

FOREIGN PATENT DOCUMENTS

| | | |
|---|---|---|
| DE | 42 16 880 A1 | 11/1993 |
| EP | 0 186 118 A2 | 7/1986 |
| EP | 0 348 737 A1 | 1/1990 |
| IT | 1224249 B1 | 9/1990 |
| JP | 07 010713 A1 | 1/1995 |
| WO | WO-95/28839 | 11/1995 |
| WO | WO-96/13163 | 5/1996 |
| WO | WO-96/17519 | 6/1996 |
| WO | WO-00/16627 | 3/2000 |
| WO | WO 01/89301 | 11/2001 |

OTHER PUBLICATIONS

Derwent English Language abstract of DE 42 16 880 A1.
Derwent English Language abstract of JP 07010713A.
Derwent English Language abstract of IT 1224249.

*Primary Examiner*—S. Mark Clardy
(74) *Attorney, Agent, or Firm*—Connolly Bove Lodge & Hutz LLP

(57) ABSTRACT

The invention relates to a composition comprising (a) 2-(2'-nitro-4'-methylsulfonylbenzoyl)-1,3-cyclohexanedione, or an agriculturally acceptable salt or metal complex thereof; and (b) N-isopropyl-(5-trifluoromethyl-1,3,4-thiadiazol-2-yl)-4-(4'-fluoro-oxycetanilide); and their use as herbicides.

15 Claims, No Drawings

HERBICIDAL COMPOSITIONS

This invention relates to new compositions comprising an N-isopropylheteroaryloxyacetanilide herbicide and a benzoylcyclohexanedione derivative, and to their use as herbicides.

The compounds of the invention are known in the art. N-isopropylheteroaryloxyacetanilides are described in European Patent Publication Number 0348737, published on 3 Jan. 1990, which in particular discloses N-isopropyl-(5-trifluoromethyl-1,3,4-thiadiazol-2-yl)-(4'-fluoro-oxyacetanilide) as compound 34. Benzoyl cyclohexanediones are described in for example European Patent Publication No. 0186118. U.S. Pat. No. 5,506,196, specifically discloses 2-(2'-nitro-4'-methylsulfonylbenzoyl)-1,3-cyclohexanedione. Both of these publications teach that these compounds possess herbicidal activity. However, neither of the publications teach specific anti-gramineous properties in the compounds. EP-A1-0348737 teaches that the acetanilide compounds may be applied at from 0.01 to 10 kg of active compound per hectare of soil surface, preferably 0.05 to 5 kg per ha; no details of the precise dose rates used for the application of the compounds to treat graminea. U.S. Pat. No. 5,506,196 teaches that the compounds of the invention possess high activity in comparison with known compounds against certain weed species.

Hence the literature does not teach mixtures of these compounds; nor does it suggest that such a mixture would be expected to be particularly useful as an anti-graminicide. At present the most commonly used mixture in this area of weed science comprises metolachlor and atrazine. These are frequently recommended for use at dose rates from 1 to 2.5 kg/ha of metolachlor and from 0.5 to 2.5 kg/ha of atrazine. An object of the invention is thus to provide a mixture suitable as a graminicide which may be used at reduced dose rates of active compound in comparison with the known products.

It has been found that the mixture of N-isopropyl-(5-trifluoromethyl-1,3,4-yl)-4-(4'-fluoro-oxyacetanilide) with 2-(2'-nitro-4'-m thylsulfonylbenzoyl)-1,3-cyclohexanedione provides effective control of an extremely wide range of both monocotyledon and dicotyledon weeds at reduced dose rates when compared with these known compounds. Moreover it provides effective control together with selectivity in important crop species such as maize.

In addition to this, it has been found that in certain conditions the combined herbicidal activity of 2-(2'-nitro-4'-methylsulfonylbenzoyl)-1,3-cyclohexanedione with N-isopropyl-(5-trifluoromethyl-1,3,4-thiadiazol-2-yl)-4-(4'-fluoro-oxyacetanilide) for the control of certain weed species e.g. *Setaria viridis*, *Echinochioa crus-gall*, *Amaranthus retroflexus* and *Polygonum lapathifollum*, is greater than expected, without an unacceptable increase. In crop phytotoxicity.

This unexpected effect gives improved reliability in controlling these competitive weeds of many crop species, and contributes to a considerable reduction in the amount of active ingredient required for weed control.

According to the present invention there is provided a method for controlling the growth of weeds at a locus which comprises applying to said locus a herbicidally effective amount of:

(a) a benzoyl cyclohexanedione of formula (I):

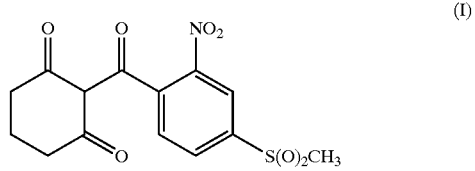

which is 2-(2'-nitro-methylsulfonylbenzoyl)-1,3-cyclohexanedione or an agriculturally acceptable salt of metal complex thereof; and (b) N-isopropyl-(5-trifluoromethyl-1,3,4-thiadiazol-2-yl)-4-(4'-fluoro-oxyacetanilide) having the formula (II):

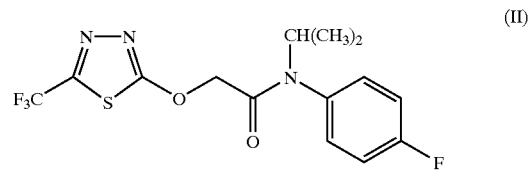

For convenience N-isopropyl-(5-trifluoromethyl-1,3,4-thiadiazol-2-yl)-4'-(4'-fluoro-oxyacetanilide) is hereafter referred to as compound B.

The amounts of 2-(2'-nitro-methylsulfonylbenzoyl)-1,3-cyclohexanedione and compound B applied vary depending on the weeds present and their population, the compositions used, the timing of the application, the climatic and edaphic conditions, and (when used to control the growth of weeds in crop growing areas) the crop to be treated. In general, taking these factors into account, application rates from 0.5 g to 512 g of benzoyl cyclohexanedione and from 10 to 10000 g of compound B per hectare give good results. However, it will be understood that higher or lower application rates may be used, depending upon the problem of weed control encountered.

The method of the invention is most preferably used for the control of weeds at a locus used, or to be used for the growing of a crop. When applied to a crop-growing area, the rate of application should be sufficient to control the growth of weeds without causing substantial permanent damage to the crop.

Crops which the mixture may be used with include soyabeans, sugarcane, cotton, maize, sunflower, peas, chickpeas, potatoes, sorghum rice and cereals. The preferred crop, in terms of the selectivity of the mixture, is maize. For the selective control of weeds at a locus of weed infestation which is an area used, or to be used, for growing of crops application, rates from 5 g to 512 g of benzoyl cyclohexanedione and from 50 to 5000 g of compound B per hectare are particularly suitable, preferably from 20 g to 200 g of benzoyl cyclohexanedione and from 80 g to 875 g of compound B per hectare, most preferably from 25 g to 150 g (about 80 g being most preferred) of benzoyl cyclohexanedione and from 300 g to 500 g (360 g being most preferred under humid conditions and 450 g under more dry conditions) of compound B per hectare.

The mixture is preferably applied pre-emergence but can also be applied post-emergence (especially at an early stage of weed growth). By the term 'pre-emergence application' is meant application to the soil in which the weed seeds or seedlings are present before emergence of the crop. One example of a pre-emergence application is known as 'pre-plant incorporated' (PPI), where the herbicide is incorporated into the soil before planting the crop. Early PPI application may also be used. The mixture may also be applied pre-planting (i.e. before the crop is planted) either to the surface of the soil or soil-incorporated. Early pre-plant treatments using the mixture (particularly surface applied) are also a feature of the method of the invention.

According to a further feature of the present invention there are provided herbicidal compositions comprising:
(a) 2-(2'-nitro-4'-methylsulfonylbenzoyl)-1,3-cyclohexanedione or an agriculturally acceptable salt or metal complex thereof; and
(b) N-isopropyl-(5-trifluoromethyl-1,3,4-thiadiazol-2-yl)-4'-(4'-fluoro-oxyacetanilide);

in association with, and preferably homogeneously dispersed in, a herbicidally acceptable diluent or carrier and/or surface active agent.

The term "herbicidal composition" is used in a broad sense, to include not only compositions which are ready for use as herbicides but also concentrates which must be diluted before use. Preferably, the compositions contain from 0.05 to 90% by weight of benzoyl-1,3-cyclohexanedione and compound B.

Unless otherwise stated, the percentages and ratios appearing in this specification are by weight.

Generally a composition in which the ratio of (a):(b) is from 1:20000 to 50:1 wt/wt (or from 1:20000 to 51.2:1 wt/wt) is used, proportions from 1000:1 to 10:1 wt/wt (or from 1000:1 to 10.24:1 wt/wt) being preferred, with proportions from 1:45 to 2.5:1 wt/wt (or from 1:43.75 to 2.5:1 wt/wt) being more preferred, and proportions from 1:20 to 2:1 wt/wt being especially preferred; ratios of 1:14 to 1:16 wt/wt (or of about 1:14 wt/wt) in humid conditions and of 1:17 to 1:20 wt/wt (or of about 1:18 wt/wt) in dry conditions being most preferred.

The preferred formulation according to the invention is in the form of a water dispersible granule, although it will be understood that other formulation types known in the art may also be used.

In accordance with the usual practice, a tank mix may be prepared prior to use by combining separate formulations of the individual herbicidal components.

According to a further feature of the present invention, there is provided a product comprising:
(a) 2-(2'-nitro-4'-methylsulfonylbenzoyl)1,3-cyclohexanedione or an agriculturally acceptable salt or metal complex thereof; and
(b) N-isopropyl-(5-trifluoromethyl-1,3,4-thiadiazol-2-yl)-4'-(4'-fluoro-oxyacetanilide);

as a combined preparation for simultaneous, separate or sequential use in controlling the growth of weeds at a locus.

The following non-limiting experiments illustrate the present invention.

Experiment 1

Seed of various broad-leaf and grass weed species were sown in unsterilised clay loam soil. The soil surface was then sprayed with ranges of concentrations of either the individual herbicide or mixtures of the two herbicides in various proportions dissolved in a mixture of acetone and water. The said weeds are *Abutilon thophrasti, Amaranthus retroflexus, Chenopodium album, Digitaria sanguinalis, Echinochloa crus-galli, Ipomoea lacunosa, Panicum millaceum, Polygonum convolvulus, Polygonum lapathifollum, Setaria faberi, Setaria viridis, Sorghum vulgare* and *Xanthium strumarium*.

Two weeks after treatment the percent reduction in plant growth, compared to an untreated control, was assessed.

Experiment 2

Seed of various weed species, as listed in Example 1, were sown and grown up to a 1–3 leaves stage. Post-emergence applications of a range of concentrations of either the individual herbicide or mixtures of two herbicides in various proportions dissolved in a mixture of acetone and water were made.

Two weeks after treatment the percent reduction in plant growth, compared to an untreated control, was assessed.

In both cases an effective level of weed control against a number of weed species, at substantially reduced application rates of active ingredient was observed.

What is claimed is:

1. A method for controlling the growth of weeds at a locus which comprises applying to said locus a herbicidally effective amount of:
(a) 2-(2'-nitro-4'-methylsulfonylbenzoyl)-1,3-cyclohexanedione or an agriculturally acceptable salt or metal complex thereof; and
(b) N-isopropyl-(5-trifluoromethyl-1,3,4-thiadiazol-2-yl)-4'-(4'-fluoro-oxyacetanilide) having the formula (II):

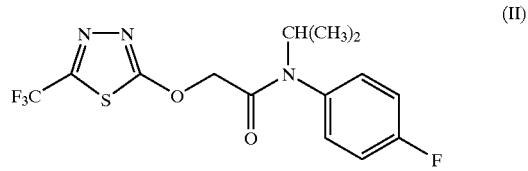

2. The method according to claim 1 using an application rate of from 0.5 g to 512 g per hectare of 2-(2'-nitro-4'-methylsulfonylbenzoyl)-1,3,4-cyclohexanedione and from 10 to 10000 g per hectare of N-isopropyl-(5-trifluoromethyl-1,3,4-thiadiazol-2-yl)-4-(4'-fluoro-oxyacetanilide).

3. The method according to claim 1, wherein the locus is used, or to be used, for the growing of a crop.

4. The method according to claim 3 wherein the crop is maize.

5. The method according to claim 1, wherein from 5 g to 512 g per hectare of 2-(2'-nitro-4'-methylsulfonylbenzoyl)-1,3-cyclohexanedione and from 50 g to 5000 g per hectare of N-isopropyl-(5-trifluoromethyl-1,3,4-thiadiazol-2-yl)-4-(4'-fluoro-oxyacetanilide) are applied to said locus.

6. The method according to claim 1, wherein from 20 g to 200 g per hectare of 2-(2'-nitro-4'-methylsulfonylbenzoyl)-1,3-cyclohexanedione and from 80 to 875 g per hectare of N-isopropyl-(5-trifluoromethyl-1,3,4-thiadiazol-2-yl)-4-(4'-fluoro-oxyacetanilide) are applied to said locus.

7. The method according to claim 1, wherein from 25 to 150 g per hectare of 2-(2'-nitro-4'-methylsulfonylbenzoyl)1,3-cyclohexanedione and from 300 to 500 g per hectare of N-isopropyl-(5-trifluoromethyl-1,3,4-thiadiazol-2-yl)-4-(4'-fluoro-oxyacetanilide) are applied to said locus.

8. The method according to claim 1, wherein (a) and (b) are applied to said locus by pre-emergence application.

9. A herbicidal composition comprising:
(a) 2-(2'-nitro-4'-methylsulfonylbenzoyl)-1,3-cyclohexanedione or an agriculturally acceptable salt or metal complex thereof; and
(b) N-isopropyl-(5-trifluoromethyl-1,3,4-thiadiazol-2-yl) 4(4'-fluoro-oxyacetanilide);

in association with a herbicidally acceptable diluent or carrier and/or surface active agent.

10. The composition according to claim 9 in which the weight ratio of (a):(b) is form 1:20,000 to 55:1.

11. The composition according to claim 9 in which the weight ratio of (a):(b) is from 1:1000 to 10:1.

12. The composition according to claim 9 In which the weight ratio of (a):(b) is from 1:45 to 2.5:1.

13. The composition according to claim 9 in which the weight ratio of (a):(b) is from 1:20 to 2:1.

14. The composition according to claim 9, wherein said composition is in the form of a water dispersible granule.

15. A product comprising a herbicidally effective amount of:

(a) 2-(2'-nitro-4'-methylsulfonylbenzoyl)-1,3-cyclohexanedione or an agriculturally acceptable salt or metal complex thereof; and (b) N-isopropyl-(5-trifluoromethyl-1,3,4-thiadiazol-2-yl)-4-(4'-fluoro-oxyacetanilide);

as a combined preparation for simultaneous, separate or sequential use in controlling the growth of weeds at a locus.

* * * * *

UNITED STATES PATENT AND TRADEMARK OFFICE
CERTIFICATE OF CORRECTION

PATENT NO. : 6,878,675 B2
DATED : April 12, 2005
INVENTOR(S) : Ken Pallett et al.

It is certified that error appears in the above-identified patent and that said Letters Patent is hereby corrected as shown below:

Column 4,
Line 34, "methylsulfonylbenzoyl)-1,3,4-cyclohexanedione and from" should read
-- methylsulfonylbenzoyl)-1,3-cyclohexanedione and from --.
Lines 62 and 63, "N-isopropyl-(5-trifluoromethyl-1,3,4-thiadiazol-2-yl)4(4'-fluoro-oxyacetanilide)" should read -- N-isopropyl-(5-trifluoromethyl-1,3,4-thiadiazol-2-yl)-4-(4'-fluoro-oxyacetanilide) --.

Signed and Sealed this

Twenty-second Day of November, 2005

JON W. DUDAS
*Director of the United States Patent and Trademark Office*